(12) United States Patent
Horos et al.

(10) Patent No.: US 11,173,176 B2
(45) Date of Patent: Nov. 16, 2021

(54) MODULATORS OF VAULT RNAS FOR USE IN THE TREATMENT OF DISEASES

(71) Applicant: European Molecular Biology Laboratory, Heidelberg (DE)

(72) Inventors: Rastislav Horos, Heidelberg (DE); Matthias W. Hentze, Heidelberg (DE); Carsten Sachse, Heidelberg (DE)

(73) Assignee: European Molecular Biology Laboratory, Heidelberg (DE)

( * ) Notice: Subject to any disclaimer, the term of this patent is extended or adjusted under 35 U.S.C. 154(b) by 21 days.

(21) Appl. No.: 16/314,204

(22) PCT Filed: May 29, 2017

(86) PCT No.: PCT/EP2017/062912
§ 371 (c)(1),
(2) Date: Dec. 28, 2018

(87) PCT Pub. No.: WO2018/001666
PCT Pub. Date: Jan. 4, 2018

(65) Prior Publication Data
US 2019/0201435 A1    Jul. 4, 2019

(30) Foreign Application Priority Data
Jun. 28, 2016   (EP) .................................. 16176740

(51) Int. Cl.
| | | |
|---|---|---|
| A61K 48/00 | (2006.01) | |
| C07H 21/04 | (2006.01) | |
| A61K 31/712 | (2006.01) | |
| C12N 15/113 | (2010.01) | |
| C12N 15/11 | (2006.01) | |
| A61P 43/00 | (2006.01) | |
| G01N 33/50 | (2006.01) | |

(52) U.S. Cl.
CPC ............ *A61K 31/712* (2013.01); *A61P 43/00* (2018.01); *C12N 15/11* (2013.01); *C12N 15/113* (2013.01); *G01N 33/5008* (2013.01); *C12N 2310/11* (2013.01); *C12N 2310/113* (2013.01); *C12N 2310/3231* (2013.01)

(58) Field of Classification Search
CPC .......................... C12N 15/113; C12N 2310/11
See application file for complete search history.

(56) References Cited

U.S. PATENT DOCUMENTS

2010/0233730 A1    9/2010   White et al.

OTHER PUBLICATIONS

Stadler et al. (Molecular Biology and Evolution, vol. 26, Issue 9, Sep. 2009, pp. 1975-1991).*
Jepsen et al. (Curr Opin Drug Discov Devel., 2004, 7(2), 188-194).*
International Search Report and Written Opinion, International Patent Application No. PCT/EP2017/062912, dated Aug. 31, 2017 (15 pages).
Cha-Molstad et al., "A,ino-terminal arginylation targets endoplasmic reticulum, chaperone BiP for autophagy through p62 binding", Nature Cell Biology, vol. 17, No. 7, Jul. 1, 2015, pp. 917-929.
Amort et al., "Expression of the vault RNA protects cells from undergoing apoptosis", Nature Communications, vol. 6, May 8, 2015, p. 7030.
Itakura et al., "p62 targeting to the autophagosome formation site requires self-oligomerization but not LC3 binding", The Journal of Cell Biology, vol. 192, No. 1, Jan. 10, 2011, pp. 17-27.
Frake et al., "Autophagy and neurodegeneration", Journal of Clinical Investigation, vol. 125, No. 1, Jan. 2, 2015, pp. 65-74.
Galluzzi et al., "Autophagy in malignant transformation and cancer progression", EMBO Journal, vol. 34, No. 7, Apr. 1, 2015, pp. 856-880.

* cited by examiner

*Primary Examiner* — Amy H Bowman
(74) *Attorney, Agent, or Firm* — Hamre, Schumann, Mueller & Larson, P.C.

(57) ABSTRACT

The present invention relates to the finding that vault RNAs (vtRNA) associate with p62, an important factor of cellular autophagy. The invention provides the modulation of the binding of vtRNA to p62 as a novel strategy to influence autophagic flux in cells. Thus, the present invention provides inhibitors of vtRNA for use in the treatment of diseases associated with a pathological reduced or insufficient autophagy in cells, such as cancer and neurodegenerative disorders. Further provided are methods for screening novel therapeutic compounds modulating autophagy via the p62/vtRNA axis.

Figure 2:
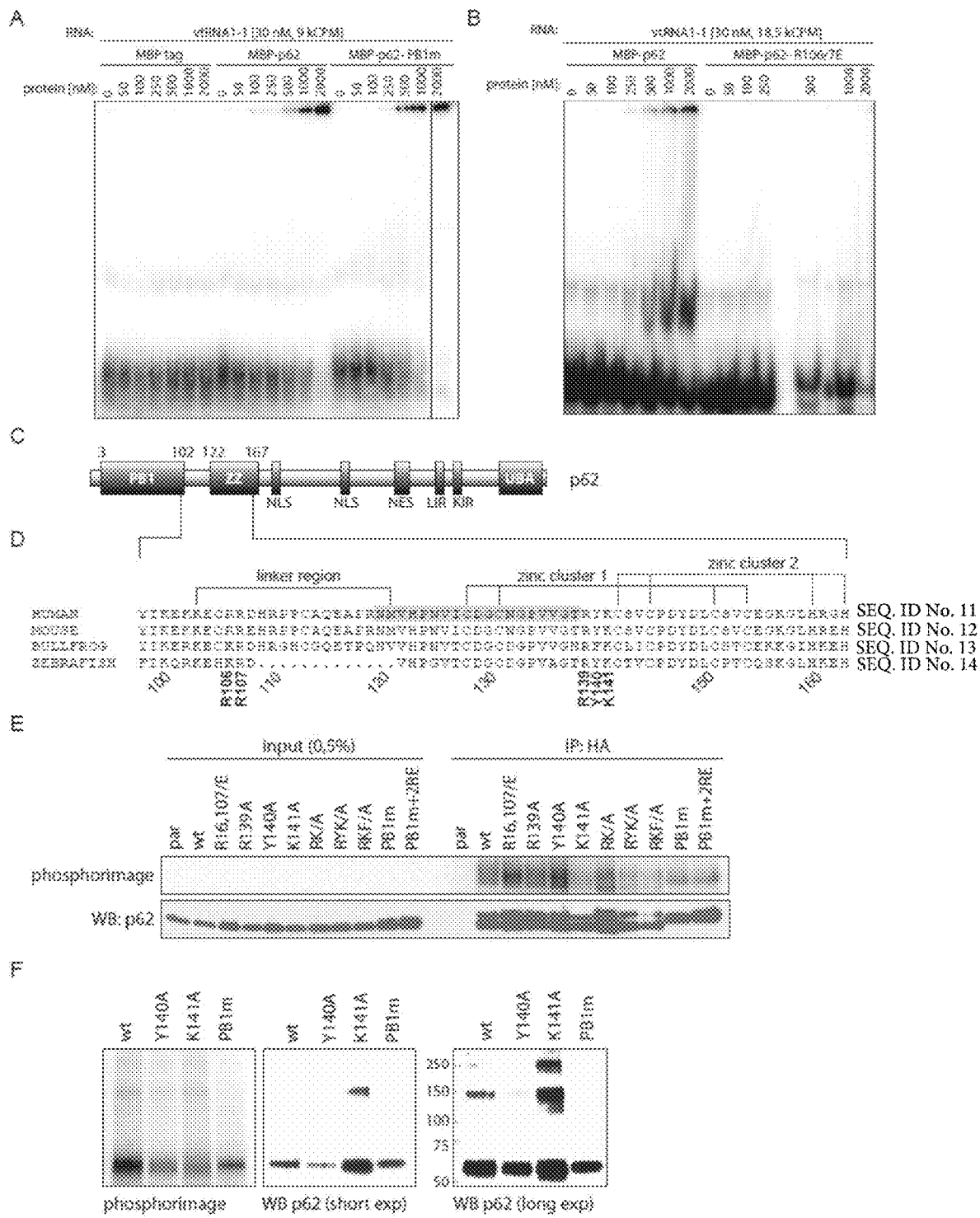

6 Claims, 6 Drawing Sheets
Specification includes a Sequence Listing.

Figure 1:
A
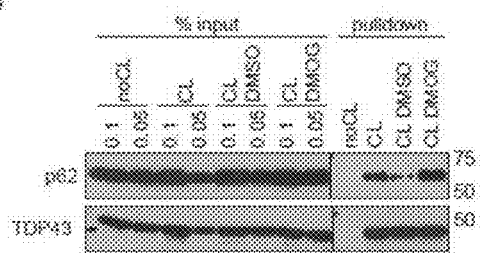
B
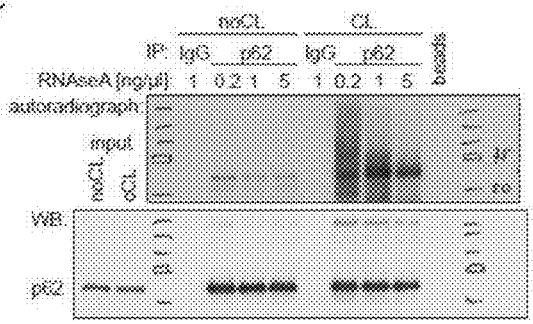
C
D
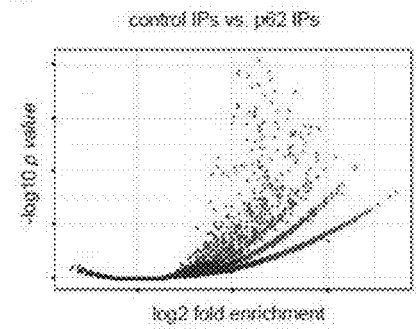
E
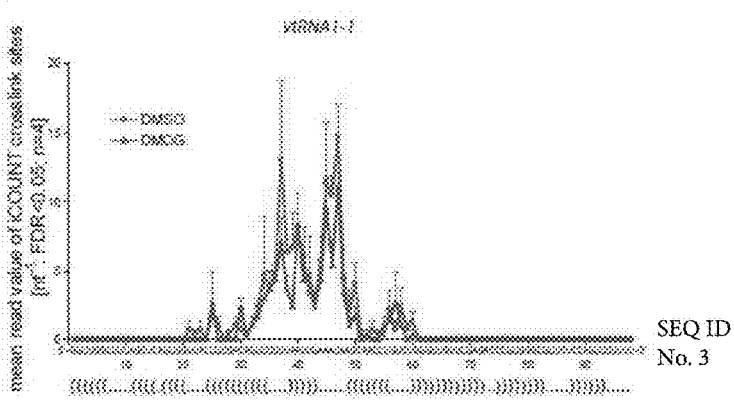
SEQ ID No. 3

Figure 4:

DNA:

```
vtRNA1-1 (98)   5'-GGCTGGCTTTAGCTCAG--CGGTTACTTCGACAGTTCTTTAATTGAAACAAGCAACCTGT---CTGGGTTGTTCGAGACCCGCGGGCGCTCTCCAGTCCTTT-' SEQ. ID No. 7
vtRNA1-2 (88)   5'-GGCTGGCTTTAGCTCAG--CGGTTACTTCGAGTA---CATTG-------TAACCACCTCT---CTGGTGTTCGAGACCCGCGGGTGCTTTCCAGCTCTTT-' SEQ. ID No. 8
vtRNA1-3 (88)   5'-GGCTGGCTTTAGCTCAG--CGGTTACTTCGGCGTG-TCAT--------CAAACCACCTCT---CTGGGTTGTTCGAGACCCGGGGGGCTCTCCAGCCCTCT-' SEQ. ID No. 9
vtRNA2-1 (100)  5'-GGGTCGGAGTTAGCTCAAGCGGTTACCTCCTCCATGCGGGACTTTCTATCCGTCCATCTGTGGG--GTTCGAAGACCCGCGGGTGCTTACTGACCCTTT-' SEQ. ID No. 10
                   **  **.  *******.   ******** **  *     *             *.* *.. *** ;*   ***;  **.. *                         
```

RNA:

```
vtRNA1-1 (98)   5'-GGCUGGCUUUAGCUCAG--CGGUUACUUCGACAGUUCUUUAAUUGAAACAAGCAACCUGU---CUGGGUUGUUCGAGACCCGCGGGCGCUCUCCAGUCCUUU-' SEQ. ID No. 3
vtRNA1-2 (88)   5'-GGCUGGCUUUAGCUCAG--CGGUUACUUCGAGUA---CAUUG-------UAACCACCUCU---CUGGUGUUCGAGACCCGCGGGUGCUUUCCAGCUCUUU-' SEQ. ID No. 4
vtRNA1-3 (88)   5'-GGCUGGCUUUAGCUCAG--CGGUUACUUCGGCGUG-UCAU--------CAAACCACCUCU---CUGGGUUGUUCGAGACCCGGGGGGCUCUCCAGCCCUCU-' SEQ. ID No. 5
vtRNA2-1 (100)  5'-GGGUCGGAGUUAGCUCAAGCGGCCAAGCGGUUACCUCCUCAUGCGGGACUUUCUAUCCGUCCAUCUGUGGG--GUUCGAAGACCCGCGGGUGCUUACUGACCCUUU-' SEQ. ID No. 6
                   **  **.  *******.   ******** **  *     *             *.* *.. *** ;*   ***;  **.. *                         
```

MODULATORS OF VAULT RNAS FOR USE IN THE TREATMENT OF DISEASES

The present invention relates to the finding that vault RNAs (vtRNA) associate with p62, an important factor of cellular autophagy. The invention provides the modulation of the binding of vtRNA to p62 as a novel strategy to influence autophagic flux in cells. Thus, the present invention provides inhibitors of vtRNA for use in the treatment of diseases associated with a pathological reduced or insufficient autophagy in cells, such as cancer and neurodegenerative disorders. Further provided are methods for screening novel therapeutic compounds modulating autophagy via the p62/vtRNA axis.

BACKGROUND OF THE INVENTION

Macroautophagy (autophagy) is an important mechanism for targeting cellular components including proteins, protein aggregates and organelles for degradation in lysosomes. This catabolic, cellular self-digestion process is induced in response to starvation or stress, causing the formation of double membrane vesicles called autophagosomes that engulf proteins and organelles. Autophagosomes then fuse with lysosomes where the autophagosome and their cargo are degraded. This lysosome-mediated cellular self-digestion serves to recycle intracellular nutrients to sustain cell metabolism during starvation and to eliminate damaged proteins and organelles that accumulate during stress. Although elimination of individual proteins occurs by the ubiquitin-mediated proteasome degradation pathway, the autophagy pathway can eliminate protein aggregates and organelles. Thus, autophagy complements and overlaps with proteasome function to prevent the accumulation of damaged cellular components during starvation and stress. Through these functions, autophagy is an essential cellular stress response that maintains protein and organelle quality control, protects the genome from damage, and sustains cell and mammalian viability.

The core molecular machinery of autophagy is controlled by the protein products encoded by a group of ATG genes evolutionarily conserved from yeast to mammals. Nucleation of autophagic vesicles requires PtdIns3P, the product of type III PI3 kinase complex including Beclin 1 (mammalian homolog of yeast Atg6) and Vps34, as well as two ubiquitin-like molecules, Atg12 and LC3 (homolog of Atg8), which function sequentially in mediating the formation of autophagosomes. In the first ubiquitination-like reaction, Atg12 is conjugated to Atg5 and forms a large multimeric protein complex, which plays a key role in determining the nucleation of autophagosome. In the second reaction, LC3 is conjugated to phosphatidylethanolamine, resulting in membrane translocation important for the elongation and closure of autophagosome.

Autophagy dysfunction is a major contributor to diseases including, but not limited to, neurodegeneration, liver disease, and cancer. Many human neurodegenerative diseases are associated with aberrant mutant and/or polyubiquitinated protein accumulation and excessive neuronal cell death. Neurons of mice with targeted autophagy defects accumulate polyubiquitinated- and p62-containing protein aggregates that result in neurodegeneration. The human liver disease steatohepatitis and a major subset of hepatocellular carcinomas (HCCs) are associated with the formation of p62-containing protein aggregates (Mallory bodies) (Zatloukal, K., et al. (2002), p62 is a common component of cytoplasmic inclusions in protein aggregation diseases, Am. J. Pathol. 160, 255-263). Livers of mice with autophagy defects have p62-containing protein aggregates, excessive cell death, and HCC.

Autophagy has been proposed to play complex roles in the development and treatment of cancers. Activation of autophagy functions as a tumor suppression mechanism by preventing necrotic cell death and subsequent inflammation which favors tumor growth. On the other hand, inhibition of autophagy may lead to genome instability through unknown mechanisms which might explain the increased frequency of beclin 1 heterozygosity in multiple lines of cancers and decreased expression of autophagy-related proteins in malignant epithelial ovarian cancer. Thus, chronic suppression of autophagy may stimulate tumorigenesis.

The importance of autophagy in cellular garbage disposal is clear, as autophagy is the only identified mechanism for the turnover of large cellular structures such as organelles and protein aggregates. How organelles are recognized and directed to autophagosomes for degradation may involve organelle-specific processes such as mitophagy and ER-phagy that may mitigate oxidative stress emanating from dysfunctional organelles. Damaged proteins that accumulate during stress can be refolded, ubiquitinated and degraded by the proteasome pathway, or aggregated and degraded by autophagy. To direct damaged or unfolded proteins to the autophagy pathway, p62 binds to polyubiquitinated proteins forming protein aggregates by oligomerization/polymerization and to Atg8/LC3 on the autophagosome membrane to target aggregates to autophagosomes for degradation. Protein aggregation may be a protective mechanism to limit cellular exposure to toxic proteins through sequestration, as well as an efficient packaging and delivery mechanism that collects and directs damaged proteins to autophagosomes. Liver-specific autophagy defects in mice cause accumulation of p62 aggregates, elevated oxidative stress and hepatocyte cell death. Thus, without seeking to be bound by any theory or theories of operation, it is believed that the inability to dispose of p62 aggregates through autophagy may be toxic to normal tissues.

Vaults are the largest ribonucleotide-protein complexes identified in mid-1980's (Kedersha and Rome, 1986). Vaults are found in a wide spectrum of Eukaryotes, but are missing e.g. in fruit fly, roundworm or yeast (Stadler et al., 2009). Although vaults have been linked to various cellular processes like drug resistance, apoptosis or nuclear transport (Berger et al., 2009), their precise function still remains obscure. Barrel-shaped vaults comprise of three proteins—major vault protein (MVP) that confers the major vault structure, telomerase associated proteins 1 (TEP1), an RNA binding protein thought to be located at the caps of the vaults, and poly-A-ribose polymerase 4 (PARP4), located inside of the particle. Additionally, vaults contain small non-coding vault RNA (vtRNA), which is predicted to be located at the caps of the complex bound by TEP1 (Kong et al., 2000). Humans have 4 vtRNA paralogs (vtRNA1-1, vtRNA1-2, vtRNA1-3, vtRNA2-1), which are 88-100 nt long, transcribed by RNA Pol III and encoded on 5q chromosome. Sedimentation experiments suggested that only minority of total vtRNA pool is incorporated into vaults (Nandy et al., 2009). Overexpression of vtRNA1-1 was shown to be protective against apoptosis in a cellular model of EBV infection (Amort et al., 2015) and to favor influenza virus replication via PKR deactivation (Li et al., 2015). Yet, the precise function of vault RNA within or outside vaults also remains largely undefined.

Still, there are insufficient therapeutic approaches targeting autophagy as a major contributor for many human disorders. It is therefore an object of the present invention to provide new approaches for the targeted modulation of autophagy in cells to allow treatment of neurodegenerative and cancer diseases.

As used herein, the term "vault" or "vault particle" refers to a large cytoplasmic ribonucleoprotein (RNP) particle found in eukaryotic cells. The vault or vault particle is composed of MVP, VPARP, and/or TEP1 proteins and one or more untranslated vtRNA molecules. Human vaults comprise vtRNA1-1, vtRNA1-2, vtRNA1-3 and vtRNA2-1.

The terms "vault RNA" and "vtRNA" refer to non-protein-coding RNA molecules found to be associated or contained within a vault.

The term "autophagy" refers to the catabolic process involving the degradation of a cell's own components; such as, long lived proteins, protein aggregates, cellular organelles, cell membranes, organelle membranes, and other cellular components. The mechanism of autophagy may include: (i) the formation of a membrane around a targeted region of the cell, separating the contents from the rest of the cytoplasm, (ii) the fusion of the resultant vesicle with a lysosome and the subsequent degradation of the vesicle contents. For example, the term autophagy may refer to one of the mechanisms by which a starving cell re-allocates nutrients from unnecessary processes to more essential processes. Also, for example, autophagy may inhibit the progression of some diseases and play a protective role against infection by intracellular pathogens.

The term "autophagy associated disease" includes a disease that can be treated by the induction or reduction of autophagy. Examples of such diseases include diseases caused by misfolded protein aggregates. The term "disease caused by misfolded protein aggregates" is intended to include any disease, disorder or condition associated with or caused by misfolded protein aggregates. For example, such diseases include Alzheimer's disease, Parkinson's disease, amyotrophic lateral sclerosis, Huntington's disease, spinocerebellar ataxia, oculopharyngeal muscular dystrophy, prion diseases, fatal familial insomnia, alpha-1 antitrypsin deficiency, dentatorubral pallidoluysian atrophy, frontal temporal dementia, progressive supranuclear palsy, x-linked spinobulbar muscular atrophy, and neuronal intranuclear hyaline inclusion disease. The term "autophagy associated disease" also includes cancer e.g., any cancer wherein the induction of autophagy would inhibit cell growth and division, reduce mutagenesis, remove mitochondria and other organelles damaged by reactive oxygen species or kill developing tumor cells. Autophagy associated diseases can be chronic diseases.

As used herein, the term "autophagic flux" refers to autophagic turnover i.e., the rate of formation and clearance of autophagosomes (APs).

In a first aspect the above problem is solved by a method for modulating autophagy in a cell, comprising a step of inhibiting or increasing the interaction of a vault RNA (vtRNA) and p62 in the cell, alternatively of the interaction between a vault and p62.

A vtRNA according to the invention is preferably selected from the group comprising, vtRNA1-1, and vtRNA1-2, vtRNA1-3 and vtRNA2-1; preferably vtRNA1-1, and vtRNA1-2, and vtRNA2-1, and most preferably the vtRNA is vtRNA1-1. It is understood that depending on the organism the skilled person may select other vtRNA homologs found in the respective species. The SEQ ID NO: 3 to 6 show human sequences, but in particular for screening purposes also mouse or rat or other mammalian vtRNAs may be subject of the present invention.

The present invention surprisingly discovered a function of the autophagy involved protein p62 as an RNA binding protein. p62 was until now not known to bind RNA, and in particular it is a new development that RNAs from vaults bind p62 and modulate its functions. p62 is also known as SQSTM1 (Sequestosome 1).

The interaction between p62 and the vault or vtRNA is a binding of the vtRNA (as such or in context of a vault complex) to the p62 protein. The binding of a vault or vtRNA to p62 may, if intended, be determined by a method as disclosed herein in the example section.

In a further additional or alternative preferred embodiment of the invention the modulation of autophagy is a modulation of the autophagy flux in the cell. The autophagic flux is preferably determined by monitoring the modulation of the conjugation of LC3B and/or the formation of p62 punctae in the cell. Microtubule-associated protein 1A/1B-light chain 3 (LC3) is a soluble protein with a molecular mass of approximately 17 kDa that is distributed ubiquitously in mammalian tissues and cultured cells. During autophagy, autophagosomes engulf cytoplasmic components, including cytosolic proteins and organelles. Concomitantly, a cytosolic form of LC3 (LC3-I) is conjugated to phosphatidylethanolamine to form LC3-phosphatidylethanolamine conjugate (LC3-II), which is recruited to autophagosomal membranes. Also, during autophagy, self-oligomerization of p62 promotes protein aggregate formation which is observed as punctae and therefore may be used as a marker for autophagic flux.

In the present invention there will be embodiments in which it is preferred to increase the autophagic flux in a cell. Increasing the autophagic flux is preferably achieved by inhibiting the interaction of a vault RNA (vtRNA) and p62 in the cell.

Yet, in other preferred embodiments of the present invention, it will be preferably to decrease the autophagic flux in the cell. A decrease of the autophagic flux in context of the invention is achieved by increasing the interaction of a vault RNA (vtRNA) and p62 in the cell.

In some preferred embodiments of the invention the inhibiting or enhancing the interaction of a vtRNA and p62 in the cell is accomplished by contacting said cell with an antagonist or agonist of the expression, function or stability of a vtRNA. It is also encompassed that inhibiting or increasing the interaction of a vtRNA and p62 in the cell is accomplished by contacting said cell with a substance capable of (competitively) disturbing, or enhancing respectively, the binding between the vtRNA and p62. Such a disturber of the binding is preferably a substance which binds to a region of p62 located close to or around the amino acid positions R139 and/or K141 in p62 (human p62; the respective sequence positions in other mammals can be derived from sequence alignments). The region is preferably 100 amino acids long, more preferably about 50, 30, 20, 15, or 5 to 10 amino acid positions long and comprises R139 and/or K141 of (human) p62 (in other homologs the respective corresponding positions).

Substances that will increase the interaction of a vtRNA or vault and p62 are preferably referred to as enhancers of the interaction of a vtRNA or vault and p62 in context of the present disclosure. An enhancer of the invention is any substance that could induce an increased binding of a vault or vtRNA to p62. Preferably such a compound has an effect as an antagonist of autophagy according to the finding of the invention that inhibiting the interaction between a vtRNA and p62 results in an increased autophagic flux.

Such an enhancing substance may be selected from an oligonucleotide, modified oligonucleotide, antibody, small molecule, ribozyme, peptide or recombinant protein. Preferred examples of an enhancer of the interaction of a vtRNA and p62 are vtRNA mimic oligonucleotides, or vtRNA expression constructs that in a cell allow the increase of the level of vtRNA and therefore, an increased binding of vtRNA to p62. An enhancer of the interaction of a vtRNA and p62 preferably may comprise a nucleotide sequence comprising a vtRNA sequence, or a modified vtRNA sequence having at least 50%, more preferably 60%, 70%, 80%, 90%, 95% most preferably 98 or 99% sequence identity of a vtRNA or a cDNA sequence of a vtRNA (for human vtRNA see SEQ ID NO: 3-6). In context of the invention a vtRNA or vtRNA mimic expression construct comprises a sequence which is a cDNA sequence of a vtRNA sequence or a vtRNA mimic or the gene sequence of a vtRNA, whereas a vtRNA molecule or vtRNA mimic molecule comprises the respective RNA sequence of these structures. The sequences of vtRNAs, respectively vtRNA genes, are well known in the art.

Expression constructs may comprise the vtRNA DNA sequence coding for the respective vtRNA and which are preferably operably linked to a promoter for the expression of vtRNA sequences. Such expression constructs are well known and may be any vector, plasmid or other nucleic acid based construct suitable for the expression of foreign DNA in cells.

In other embodiments the invention provides, or relates to, substances for inhibiting the interaction of a vtRNA or vault with p62. Such substances are referred to in the following as inhibitors of the interaction of a vtRNA or vault and p62. An inhibitor of the invention is any substance that could induce a reduced binding of a vault or vtRNA to the p62 protein. Preferably such a compound has an effect as an agonist of autophagy according to the finding of the invention that inhibiting the interaction between a vtRNA and p62 results in an increased autophagic flux in the cell.

Preferably such an inhibitor of the interaction of a vtRNA or vault and p62 is an antagonist of a vtRNA. Preferred antagonists are antisense nucleic acids or antisense molecules targeting the sequence of the vtRNA. The term "antisense molecule" in accordance with the present invention thus relates to a nucleic acid molecule, preferably an RNA, DNA, RNA/DNA or LNA molecule that has a base sequence complementary to a given vtRNA, i.e. the "sense" sequence. In some embodiments an antisense molecule is a siRNA, LNA, shRNA, or another antisense RNA interfering oligonucleotide.

A particularly preferred example of an antisense molecule of the invention is an Endoribonuclease-prepared siRNA (esiRNA). An esiRNA is a mixture of siRNA oligos resulting from cleavage of a long double-stranded RNA (dsRNA) with an endoribonuclease such as *Escherichia coli* RNase III or dicer. esiRNAs are an alternative concept to the usage of chemically synthesized siRNA for RNA Interference (RNAi). An esiRNAs is the enzymatic digestion of a long double stranded RNA in vitro. For the generation of esiRNAs a cDNA of a vtRNA template may be amplified by PCR and tagged with two bacteriophage-promoter sequences. RNA polymerase is then used to generate long double stranded RNA that is complementary to the target-gene cDNA. This complementary RNA may be subsequently digested with RNase III from *Escherichia coli* to generate short overlapping fragments of siRNAs with a length between 18-25 base pairs. This complex mixture of short double stranded RNAs is similar to the mixture generated by Dicer cleavage in vivo and is therefore called endoribonuclease-prepared siRNA or short esiRNA. Hence, esiRNA are a heterogeneous mixture of siRNAs that all target the same mRNA sequence. esiRNAs lead to highly specific and effective gene silencing.

The sequence identity of the antisense molecule according to the invention in order to target a vtRNA is with increasing preference at least 75%, at least 80%, at least 85%, at least 90%, at least 95%, at least 98%, at least 99% and 100% of the vtRNA sequence. Means and methods for determining sequence identity are known in the art. Preferably, the BLAST (Basic Local Alignment Search Tool) program is used for determining the sequence identity with regard to one or more vtRNAs as known in the art. On the other hand preferred antisense molecules such as siRNAs and shRNAs of the present invention are preferably chemically synthesized using appropriately protected ribonucleoside phosphoramidites and a conventional RNA synthesizer. Suppliers of RNA synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

The ability of antisense molecules, siRNA, and shRNA to potently, but reversibly, silence vtRNA and genes in vivo makes these molecules particularly well suited for use in the pharmaceutical composition of the invention which will be also described herein below. Ways of administering siRNA to humans are described in De Fougerolles et al., Current Opinion in Pharmacology, 2008, 8:280-285. Such ways are also suitable for administering other small RNA molecules like shRNA. Accordingly, such pharmaceutical compositions may be administered directly formulated as a saline, via liposome based and polymer-based nanoparticle approaches, as conjugated or complexation pharmaceutical compositions, or via viral delivery systems. Direct administration comprises injection into tissue, intranasal and intratracheal administration. Liposome based and polymer-based nanoparticle approaches comprise the cationic lipid Genzyme Lipid (GL) 67, cationic liposomes, chitosan nanoparticles and cationic cell penetrating peptides (CPPs). Conjugated or complexation pharmaceutical compositions comprise PEI-complexed antisense molecules, siRNA, shRNA or miRNA. Further, viral delivery systems comprise influenza virus envelopes and virosomes.

The antisense molecules, siRNAs, shRNAs may comprise modified nucleotides such as locked nucleic acids (LNAs). The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers are synthesized chemically and are commercially available. The locked ribose conformation enhances base stacking and backbone pre-organization. This significantly increases the hybridization properties (melting temperature) of oligonucleotides. Particularly preferred example of siRNAs is GapmeR (LNA™ GapmeRs (Exiqon)). GapmeRs are potent antisense oligonucleotides used for highly efficient inhibition of mRNA and vtRNA function. GapmeRs contain a central stretch of DNA monomers flanked by blocks of LNAs. The GapmeRs are preferably 14-16 nucleotides in length and are optionally fully phosphorothioated. The DNA gap activates the RNAse H-mediated degradation of targeted RNAs and is also suitable to target transcripts directly in the nucleus.

Preferred antisense molecules for use as vtRNA antagonists are antisense constructs having a sequence complementary to any of the vtRNA sequences shown in SEQ ID NO: 3 to 6. Most preferred is an antisense molecule comprising, or consisting essentially of, a sequence according to SEQ ID NO: 1 or 2 (the LNA constructs used in the examples).

In accordance with a different preferred embodiment of the various aspects of the invention the inhibitor of the interaction of vtRNA or vaults and p62 of the invention may also be an aptamer, a ribozyme, an antibody, a protein drug, or a small molecule inhibitor.

The aptamer, ribozyme, antibody, protein drug, or small molecule inhibitor of this embodiment specifically bind to one or more vtRNA or vaults, thereby inhibiting the binding of the vtRNA or vault to p62. The term "aptamer" in accordance with the present invention refers to DNA or RNA molecules being either in the natural D-conformation or in the L-conformation ("spiegelmer") that have been selected from random pools based on their ability to bind other molecules. Aptamers have been selected which bind nucleic acid, proteins, small organic compounds, and even entire organisms. A database of aptamers is maintained at http://aptamer.icmb.utexas.edu/. More specifically, aptamers can be classified as DNA or RNA aptamers or peptide aptamers. Whereas the former consist of (usually short) strands of oligonucleotides, the latter consist of a short variable peptide domain, attached at both ends to a protein scaffold. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. The molecular target envisaged by the present invention is a nucleic acid, namely an vtRNA (such as SEQ ID NO 3 to 6). Hence, aptamers can be produced against the target molecule of the invention. Peptide aptamers are peptides that are designed to interfere with other protein interactions inside cells. They consist of a variable peptide loop attached at both ends to a protein scaffold. This double structural constraint greatly increases the binding affinity of the peptide aptamer) to levels comparable to an antibody's (nanomolar range). The variable loop length is typically comprised of 10 to 20 amino acids, and the scaffold may be any protein which has good solubility properties. Currently, the bacterial protein Thioredoxin-A is the most used scaffold protein, the variable loop being inserted within the reducing active site, which is a -Cys-Gly-Pro-Cys-loop in the wild protein, the two cysteins lateral chains being able to form a disulfide bridge. Peptide aptamer selection can be made using different systems, but the most used is currently the yeast two-hybrid system. Most preferred would be a peptide aptamer that binds p62 at the above indicated binding region of vtRNA binding.

Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamer's inherently low molecular weight. The rapid clearance of aptamers can be an advantage in applications such as in vivo diagnostic imaging.

Several modifications, such as 2'-fluorine-substituted pyrimidines, polyethylene glycol (PEG) linkage, etc. are available to scientists with which the half-life of aptamers easily can be increased to the day or even week time scale.

The term "ribozymes" refers to RNA molecules that act as enzymes in the absence of proteins. These RNA molecules act catalytic or autocatalytic and are capable of cleaving e.g. other RNAs at specific target sites but they have also been found to catalyze the aminotransferase activity of the ribosome. Selection of appropriate target sites and corresponding ribozymes can be done as described for example in Zaher and Unrau (2007), RNA 13 (7): 1017-1026.

Examples of well-characterized small self-cleaving RNAs are the hammerhead, hairpin, hepatitis delta virus, and in vitro-selected lead-dependent ribozymes. The organization of these small catalysts is in contrast to that of larger ribozymes, such as the group I intron.

The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic sequences for almost any target sequence can be created, provided the target sequence contains a potential matching cleavage site.

The basic principle of constructing hammerhead ribozymes is as follows: An interesting region of the RNA, which contains the GUC (or CUC) triplet, is selected. Two oligonucleotide strands, each with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences. Since the target sequence is a short RNA sequence, namely a vtRNA. Also the aptamers and ribozymes may comprise modified nucleotides, such as locked nucleic acids (LNAs).

The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments, Fd, F(ab')2, Fv or scFv fragments, single domain VH or V-like domains, such as VhH or V-NAR-domains, as well as multimeric formats such as minibodies, diabodies, tribodies, tetrabodies or chemically conjugated Fab'-multimers (see, for example, Altshuler et al., 2010, Holliger and Hudson, 2005). The term "antibody" also includes embodiments such as chimeric (human constant domain, non-human variable domain), single chain and humanized (human antibody with the exception of non-human CDRs) antibodies. Such antibodies of the invention preferably bind to p62 or a vault or vtRNA and inhibit the interaction of the vault, or vtRNA, and p62, in accordance with the invention.

The method of the first aspect of the present invention may in certain preferred embodiments be a method for enhancing autophagy in a cell. Such a method may be used for the treatment of a disease in a subject associated with a reduced or insufficient autophagic flux in a cell. More in the context of medical uses of the various aspects and embodiments of the invention will be described herein below.

A cell according to the invention is a biological cell, preferably a mammalian cell, such as a mouse, rat or human cell. The cell-type may be selected from a neuronal cell, liver cell, a tumor cell, or an immune cell, dependent on the respective application of the invention.

The methods described herein above, may be preferably selected from ex vivo or in vitro methods, or alternatively be—in particular in the medical field—in vivo practiced methods.

In a second aspect there is also provided a method for screening modulators of autophagy, the method comprising contacting a cell with a candidate compound, monitoring the interaction of a vtRNA and p62, wherein an increased interaction between a vtRNA and p62 indicates that the candidate compound is an inhibitor of autophagic flux in a cell, whereas a reduced interaction between a vtRNA and p62 indicates that the candidate compound is an enhancer of autophagic flux in the cell. Again, binding is a preferred interaction between the two molecules vtRNA/vault and p62.

The candidate compounds may be any compound and is particularly selected from a compound described herein above as an inhibitor or enhancer of the interaction of vtRNA or vaults with p62. The respective descriptions provided herein above for the first aspect of the invention shall equally apply for the second aspect.

In a third aspect there is provided a medical application of the modulators of the interaction of a vtRNA or vault with p62. Such medical applications are preferred with the compounds for use in medicine, or methods for treating a subject, comprising a step of administration of a modulator described in context of the invention to the subject. Thus, there is provided a method for treating a disease in a subject by increasing/enhancing cellular autophagy, comprising administering to the subject a therapeutically effective amount of an inhibitor of the interaction of a vault RNA (vtRNA) and p62.

In some embodiments the disease to be treated in context of the present invention has a pathology that benefits from increasing autophagy in cells affected by the disease, for example is a disease associated with a pathological accumulation of cellular components. The increase is affected in preferred embodiments by using one of the aforementioned inhibitors of the interaction of vtRNA or vaults with p62. Such inhibitors will promote autophagy and "promoting autophagy" as used herein means increasing the rate of autophagy within a cell or organism or patient as compared to the rate of autophagy in the absence the treatment. As used herein an "autophagy related disorder" is selected from cancer, stroke, sarcopenia, infection, immune system deficiencies, liver disease, neurodegenerative diseases and cardiac disorders and will be disclosed in further detail below.

Since the present invention provides a new strategy to modulate autophagy in a cell or organism, any disorders that benefit from an increase of autophagy are subject of the treatments disclosed herein. The association of autophagy with various disorders ranging from cancer to neurodegenerative disorders is well known in the art. The link between autophagy and neurodegeneration is for example in detail explained in the reference "Autophagy and neurodegeneration" by Rebecca A. Frake, Thomas Ricketts, Fiona M. Menzies, and David C. Rubinsztein, in The Journal of Clinical Investigation; Volume 125 Number 1 Jan. 2015, which is incorporated by reference in its entirety. Therefore, there is an established link in the art between the modulation of autophagy and the treatment of neurodegenerative diseases.

Preferable subjects to be treated with an inhibitor according to the invention is a subject who has been diagnosed with a neurodegenerative disease, or liver disease, or a subject who has been treated for a neurodegenerative disease, including subjects that have been refractory to the previous treatment.

The methods of the present invention may be used to treat any neurodegenerative disease. In certain embodiments, the neurodegenerative disease is a proteinopathy, or protein-folding disease. Examples of such proteinopathies include, but are not limited to, Alzheimer's disease, Parkinson's disease, Lewy Body Dementia, ALS, Huntington's disease, spinocerebellar ataxias and spinobulbar muscular atrophy. In other embodiments, the methods of the present invention can be used to treat any neurodegenerative disease. Neurodegenerative diseases treatable by the methods of the present invention include, but are not limited to, Adrenal Leukodystrophy, alcoholism, Alexander's disease, Alper's disease, Alzheimer's disease, Amyotrophic lateral sclerosis, ataxia telangiectasia, Batten disease, bovine spongiform encephalopathy, Canavan disease, cerebral palsy, cockayne syndrome, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease, multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease, spinocerebellar ataxia, spinal muscular atrophy, Steele-Richardson-Olszewski disease, Tabes dorsalis and toxic encephalopathy.

A subject in need thereof may also include, for example, a subject who has been diagnosed with a liver disease or a subject who has been treated for a liver disease, including subjects that have been refractory to previous treatment. In certain embodiments, the liver disease is a proteinopathy, or protein-folding disease. An example of such a proteinopathy is alfa1-antitrypsin deficiency. Another liver disease that can be treated by an increase of autophagy flux in a cell in accordance with the invention is steatohepatitis, such as non alcoholic steatohepatitis (NASH) in particular in order to prevent the development of liver cirrhosis and liver cancer (HCC) which are known further stages of NASH.

A subject in need thereof may also include, for example, a subject who has been diagnosed with a muscle disease or a subject who has been treated for a muscle disease, including subjects that have been refractory to previous treatment. In certain embodiments, the muscle disease is a proteinopathy, or protein-folding disease. Examples of such a proteinopathies include, but are not limited to, deficiency sporadic inclusion body myositis, limb girdle muscular dystrophy type 2B and Miyoshi myopathy.

A subject in need thereof may also include, for example, a subject who has been diagnosed with a proteinopathy, including subjects that have been refractory to previous treatment. Examples of proteinopathies include, but are not limited to Alzheimer's disease, cerebral β-amyloid angiopathy, retinal ganglion cell degeneration, prion diseases (e.g. bovine spongiform encephalopathy, kuru, Creutzfeldt-Jakob disease, variant Creutzfeldt-Jakob disease, Gerstmann-Straussler-Scheinker syndrome, fatal familial insomnia) tauopathies (e.g. frontotemporal dementia, Alzheimer's disease, progressive supranuclear palsy, corticobasal degeneration, frontotemporal lobar degeneration), frontotemporal lobar degeneration, amyotrophic lateral sclerosis, Huntington's disease, familial British dementia, Familial Danish dementia, hereditary cerebral hemorrhage with amyloidosis (Iclandic), CADASIL, Alexander disease, Seipinopathies, familial amyloidotic neuropothy, senile systemic amyloidosis, serpinopathies, AL amyloidosis, AA amyloidosis, type II diabetes, aortic medial amyloidosis, ApoAl amyloidosis, Apoll amyloidosis, ApoAIV amyloidosis, familial amyloidosis of the Finish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amylois, seminal vesical amyloid, cystric fibrosis, sickle cell disease and critical illness myopathy.

Cells in complex, multicellular eukaryotes, such as mammals, rarely experience nutrient deprivation under normal physiological conditions. However, when such cells undergo nutrient deprivation or cellular stress, autophagy is often upregulated, which enhances cell survival. Because of their rapid growth and genetic instability, cancer cells are more reliant on autophagy for survival and growth than untransformed cells (Ding et al., (2009), Mol. Cancer Ther., 8(7), 2036-2045). Additionally, autophagy is frequently activated as a survival mechanism in cancer cells in response to the cellular stress caused by chemotherapeutic agents. Autophagy inhibitors therefore can act as anti-cancer therapeutic agents either alone or in combination with other cancer treatments (Maiuri et al., (2007) Nat. Rev. Cell Biol. 8, 741-752; Amaravadi et al, (2007) J. Clin. Invest. 117, 326-336). However, in some contexts autophagy can also be tumor suppressive, in particular in the early phases of malignancy. One example is the prevention of HCC in NASH patients by using enhancers of autophagy (see above). The connection between autophagy and cancer is in detail described in "Autophagy in malignant transformation and cancer progression" Galluzzi L et al. The EMBO Journal (2015) 34, 856-880, which is also incorporated by reference herein in its entirety.

Therefore, in context of the treatment of cancer as an autophagic associated disorder, it is preferred that a prevention of the cancer, or the treatment of a very early cancer stage will involve the use of an inhibitor of the interaction between vtRNA or vaults and p62 as described in detail herein above, which will enhance autophagy. On the other side, the treatment of cancers in later stages shall comprise the use of an enhancer of the interaction between vtRNA or vaults and p62 as described in detail herein above, which will inhibit autophagy.

Cancers that may treated by methods and compositions/compounds of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangio sarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangio sarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythro leukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In certain embodiments, the methods of the present invention include the treatment of cancer comprising the administration of a modulator of the invention in combination with a chemotherapeutic agent. Any chemotherapeutic agent is suitable for use in the methods of the instant invention, particularly chemotherapeutic agents that that induce cellular stress in cancer cells. Also radiation therapy may be applied in combination with the modulators of the invention for the treatment of cancerous disorders.

Other diseases that may in therapy benefit from an enhancement of autophagy in accordance with the herein above described invention include stroke, sarcopenia, infection, immune system deficiencies, liver disease, and cardiac disorders.

There is furthermore provided a method for determining whether a candidate compound is an activator of autophagic flux in a cell, comprising inhibiting the expression of a vtRNA in a cell, contacting said cell with the candidate compound, and monitoring the change of autophagic flux in said cell, wherein an increase in autophagic flux indicates that the candidate compound is an activator of autophagic flux. In this aspect of the invention the vtRNA is selected from vtRNA2-1, vtRNA1-1, and vtRNA1-2, and preferably is vtRNA1-1. The respective candidate compounds are selected from the afore described modulators and are for example antibodies (e.g., conjugated antibodies), proteins, peptides, small molecules, RNA interfering agents, e.g., siRNA molecules, LNA, shRNA, miRNA, ribozymes, and antisense oligonucleotides or constructs.

Another aspect also provides an inhibitor of the interaction of a vault RNA (vtRNA) and p62, as described herein before, for use in medicine. Medical uses are described in detail herein above.

Furthermore provided are in another aspect a pharmaceutical composition for use in medicine, comprising an inhibitor or enhancer of the interaction of a vault RNA (vtRNA) and p62, and a pharmaceutical acceptable carrier and/or excipient. The respective compounds of the invention are already described herein above as well as the medical uses in which the pharmaceutical composition of the invention may be employed.

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of the subject agent may be determined by reference to the plasma concentrations of the agent. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

The following figures, sequences, and examples merely serve to illustrate the invention and should not be construed to restrict the scope of the invention to the particular embodiments of the invention described in the examples. All references as cited herein are hereby incorporated in their entirety by reference.

FIG. 1. Identification of p62 as RBP and analysis of p62 bound RNAs

A. Comparative interactome capture results listing fold changes of proteins with increased and decreased RNA binding upon DMOG treatment (p adj<0.05). Whole cell lysate proteomics data for the proteins are listed in right column. Bold number indicates significant change (p adj<0.05). N.A. indicates not detected.

B. HuH7 cells were treated with DMOG or control and UV-crosslinked (CL) or not (noCL). Small scale mRNA interactome capture was performed and input samples and the pulldown eluates were analyzed for protein levels.

C. Lysates from UV crosslinked (CL) or control cells were treated with RNAse A and used for immunoprecipitation followed by T4 polynucleotide kinase labeling. After SDS-PAGE, the blot was exposed overnight on film and used subsequently for Western blotting.

D. DEseq2 comparison of significant (FDR<0.05) crosslink sites on RNAs from all control and p62 IPs. The red dots are crosslink sites significantly (p adj<0.01) enriched in p62 IPs.

E. Significant (FDR<0.05) crosslink sites read values of p62 IPs displayed on vtRNA1-1 transcript sequence (n=3, mean±s.e.m.). Predicted secondary structure is displayed below the RNA sequence (dots represent single stranded regions, brackets represent double stranded regions).

FIG. 2. In vitro and in vivo interaction of p62 and RNA

A. EMSA using 32P-UTP labeled vtRNA1-1 and MBP tag only, MBP-p62 or MBP-p62 with mutations in PB1 domain.

B. EMSA using 32P-UTP labeled vtRNA1-1 and MBP-p62 or MBP-p62 with R106E/R107E mutations.

C. Scheme of the human p62 domain architecture, drawn to scale.

D. Zoom in the human p62 protein region between AA 98-163. Orthologous proteins are aligned below; dotted region in Zebrafish represents insertion of long peptide.

Linker region and putative zinc finger residues are indicated. Grey shaded peptide represents N-link peptide from RBD-map protocol. Residues used for mutational analysis are indicated below in bold.

E. Parental HuH-7 cells or stable cell lines expressing p62 in wt and mutated form were UV-crosslinked and lysed. RNAseA treated lysates were used for HA immunoprecipitation followed by T4 polynucleotide kinase labeling. After SDS-PAGE, the blot was exposed overnight on film and used subsequently for Western blotting. RK/A–R139A+ K141A; RYK/A–R139A+Y140A+K141A; RKF–R139A+ K141A+F168A; PB1m (R21A+D69A+D73A); PB1m+2RE (R21A+D69A+D73A+R106E+R107E).

F. HuH-7 cells or stable cell lines expressing p62 in wt and mutated forms were UV crosslinked and lysed. Immunoprecipitation was done with HA antibody followed by PNK labeling, elution and SDS-PAGE—The blot was exposed to phosphorimager screen and subsequently used for Western blotting.

Figure 3:
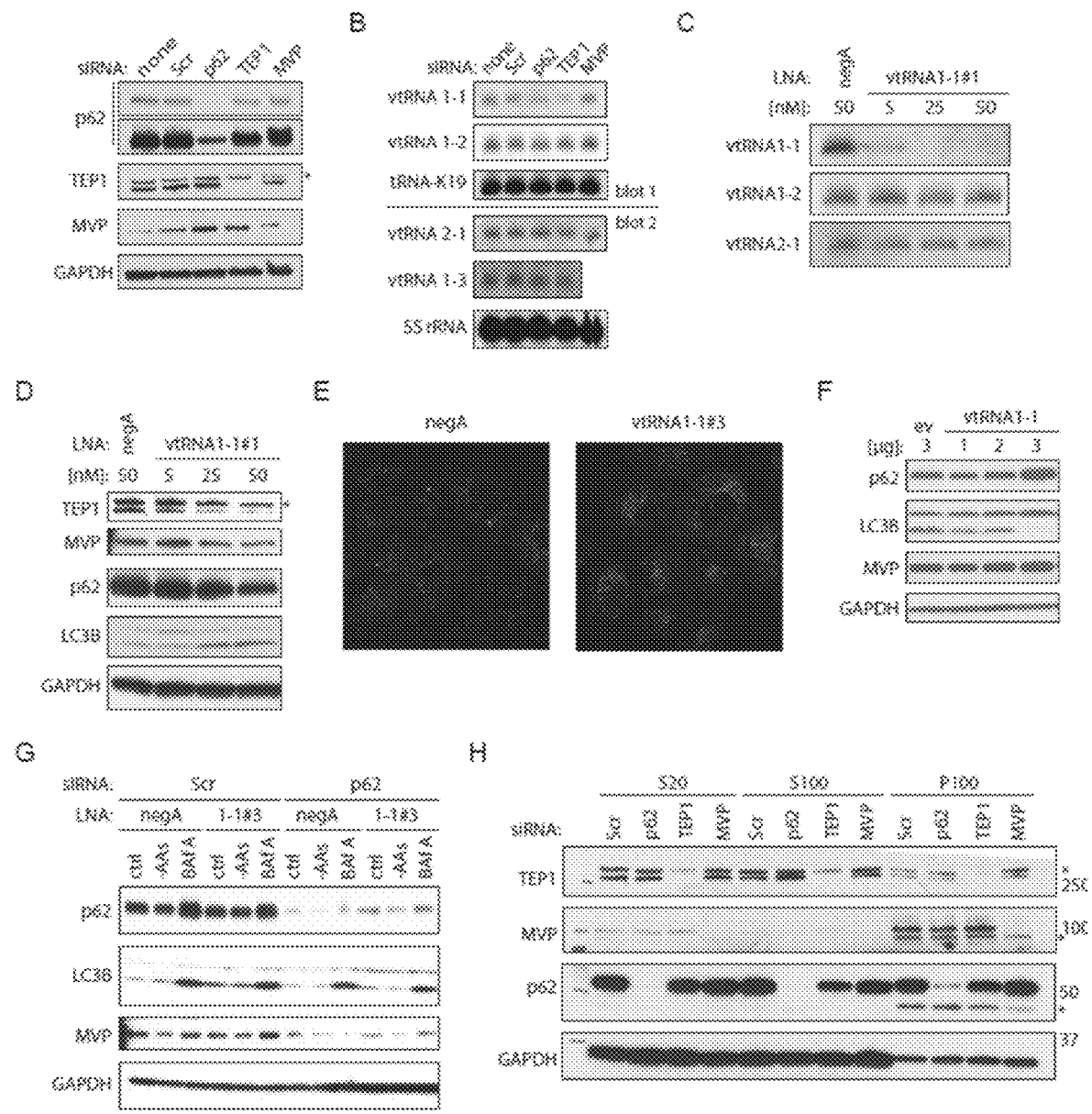

FIG. 3. Effects of vtRNA1-1 levels on autophagy flux

A. Cells were transfected with siRNA (SEQ ID NO: 1 and 2) for 72 hours then lysed and analyzed for protein levels.

B. Cells were transfected with siRNA for 72 hours, total RNA was isolated and analyzed by Northern blotting. * indicates unspecific band.

C. Cells were transfected with LNA oligos at indicated concentrations and lysed after 48 hours. Total RNA was isolated and analyzed by Northern blotting.

D. Cells were transfected with LNA oligos at indicated concentrations and lysed after 48 hours. Proteins levels were analyzed.

E. Cells were seeded on coverslips and after 24 hours transfected with indicated LNAs (50 nM). Cells were grown for further 48 hours, fixed, stained for p62 and analyzed on fluorescent microscope.

F. Cells were transfected with ev or plasmid encoding vtRNA1-1 and lysed after 24 hours. Total protein levels were analyzed.

G. Cells were transfected with indicated LNA oligos (50 nM) and siRNAs (20 nM) and incubated for 48 hours. Before lysis, cells were incubated in fresh complete media for 1 hour (ctrl), starved for serum and amino acids for 1 hour (−AA) or treated with 50 nM bafilomycine A1 for 5 hours (BafA). Lysates were analyzed for total protein levels.

H. Cells were transfected with indicated siRNA and lysed after 72 hours. Lysates were pre-cleared at 20,000×g and supernatant was saved (S20). Pellet was resuspended and subsequently centrifuged at 100,000×g. The supernatant (S100) and pellet (P100) was then used for Western blotting. * indicates unspecific bands.

FIG. 4: Alignment of vtRNA sequences

Figure 5:
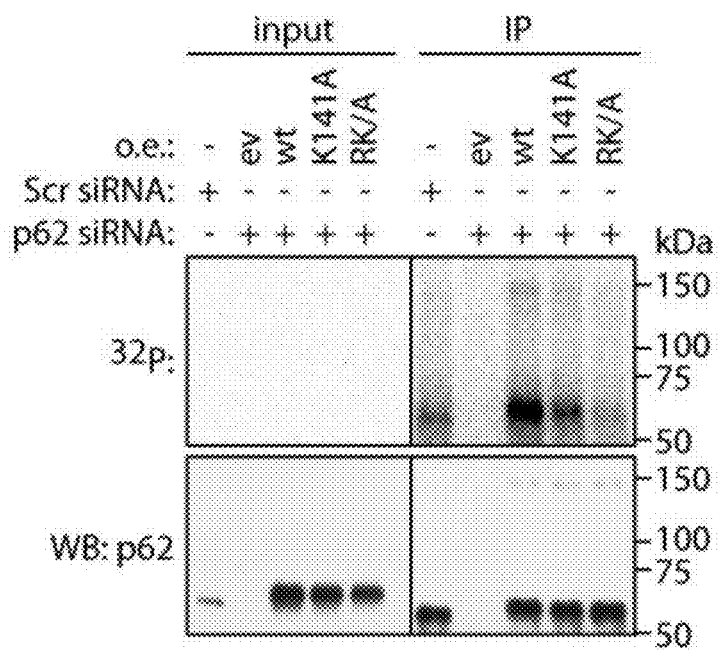

FIG. 5: HuH-7 cells treated with indicated siRNA were transfected with empty vector (ev) or p62 wt and variants (K141A, RK/A refers to the R139/K141-AA). Cells were exposed to 254 nm UV-C light, lysed and used for IP followed by the radioactive labeling of RNAs and Western blotting.

Figure 6:
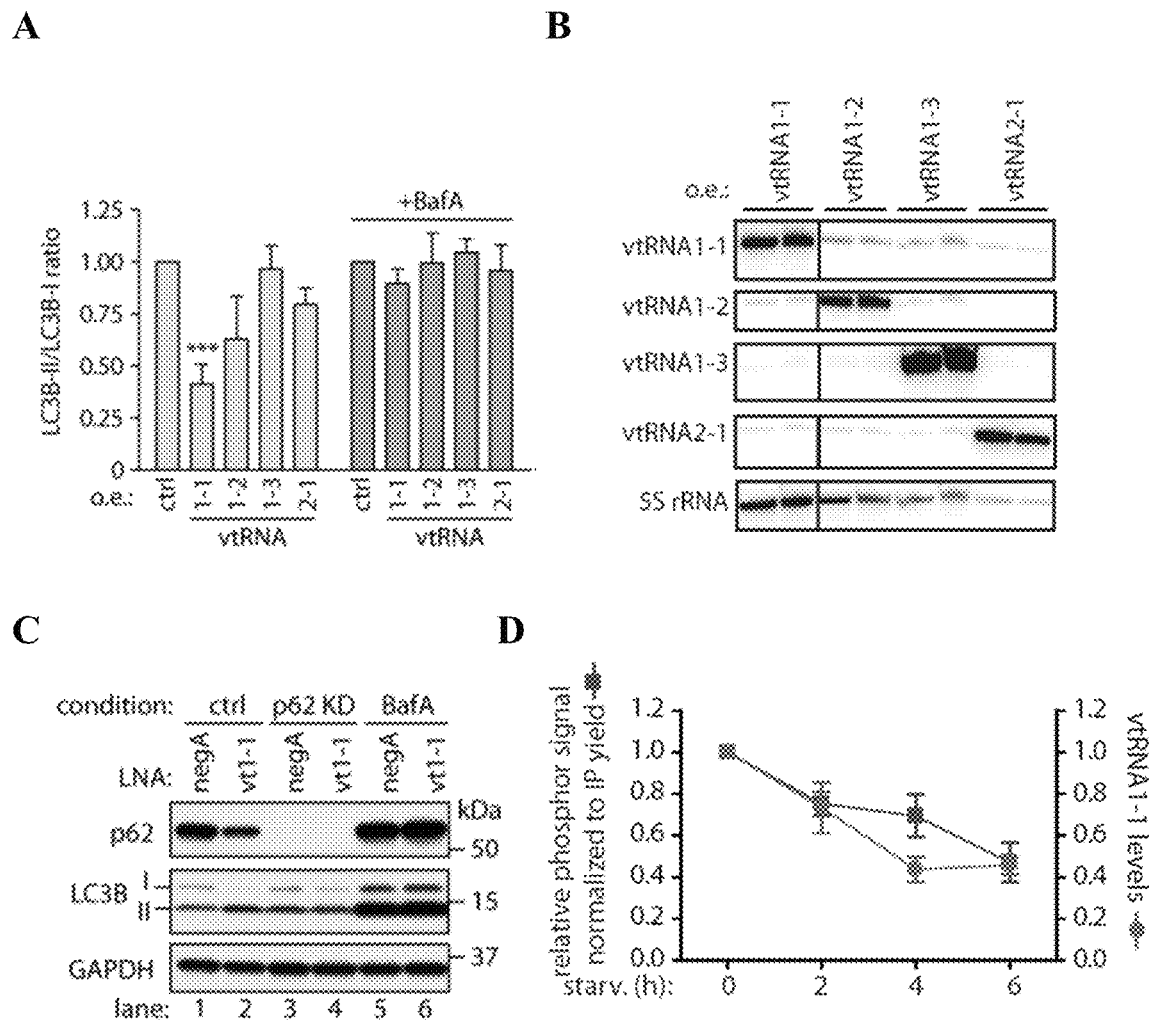

FIG. 6: vtRNA1-1 regulates autophagy via p62. (A) Cells were transfected with indicated vtRNAs, vehicle treated or treated with BafA at 100 nM for 5 hours, and then lysed. Lysates were analyzed by Western blotting and images of LC3B staining were quantified. n=3, ***p<0.005; (B) Cells were transfected with indicated vtRNAs, total RNA was isolated after 24 hours and analyzed by Northern blotting. (C) Cells were transfected with indicated LNA oligos and control or p62 siRNA and incubated for 48 hours. Where indicated, cells were treated with BafA. Lysates were analyzed by Western blotting with the indicated antibodies. (D) Cells were starved in minimal medium for the indicated time, 254 nm UV-C light exposed and lysed. Lysates were used for p62 IP and RNA radiolabeling assay. After SDS-PAGE and transfer, the membrane was exposed overnight on film and used subsequently for Western blotting. RNA binding of p62 (blue line) was quantified as ratio of radioactive signal over the immunoprecipitated protein amount. vtRNA1-1 levels were analyzed from total lysates by Northern blotting and plotted as relative to the 0 hour starvation time point (red line).

And in the Sequences:

| | |
|---|---|
| SEQ ID NO 1: | 5'-TTAAAGAACTGTCGAA-'3 (vtRNA1-1 #1) |
| SEQ ID NO 2: | 5'-TTAAAGAACTGTCGA-'3 (vtRNA1-1 #3) |
| SEQ ID NO 3: | human vtRNA1-1 |
| SEQ ID NO 4: | human vtRNA1-2 |
| SEQ ID NO 5: | human vtRNA1-3 |
| SEQ ID NO 6: | human vtRNA2-1 |
| SEQ ID NO: 7-14: | Sequences of FIGS. 2 and 4. |

EXAMPLES

Example 1: DMOG Increases p62 RNA Binding to PolIII RNA Targets

As post translational modifications (PTMs) have vast impact on the protein properties and functions (Karve and Cheema, 2011), the inventors initially set to investigate the role of hydroxylation on RNA binding activity of RBPs. For this purpose dimethyloxalylglycine (DMOG) was used as an inhibitor of prolyl-hydroxylases that require α-ketoglutarate (αKG), along oxygen and ferrous iron, for their enzymatic activity. To identify novel RBPs involved, a comparative mRNA interactome capture on cells treated with 0.5 mM DMOG for 90 min, was performed in order to prevent vast changes in RBPs binding due to the translation shutdown caused by deactivated mTORC1.

Whole cell lysate proteomics indicated vast changes in proteome, with major regulators or components of mTORC1 complex appearing among top up- (DDB1, TSC2, LAMTOR1) or down-regulated (LAMTOR2, PTEN) proteins. Comparative interactome capture uncovered RBPs involved in stress granule assembly, mRNA export and degradation, as increased in RNA binding upon DMOG treatment, whereas ribosomal proteins, translation factors and aminoacyl-synthetases displayed decreased RNA binding (FIG. 1A) and this dynamics in RBPs reflected the decrease in the protein synthesis rates. Inspection of peptide hydroxylation levels on interactome proteins peptides did not yield a difference between the DMOG and control samples (not shown), suggesting that the differential binding of those RBPs is not affected by their peptide hydroxylation dynamics.

Unexpectedly, protein with most prominent increase in RNA binding upon DMOG treatment was sequestosome 1 (also known as p62), a receptor for targeted autophagy. p62 is important autophagy protein, a process tightly controlled by mTORC1 and p62 has been described to form a complex with mTORC1 itself (Duran et al., 2011), which prompted the inventors to investigate hitherto unknown RNA binding function of p62 further.

The increase in p62 RNA binding in mRNA interactome capture eluates from DMOG treated Huh-7 cells could be confirmed by direct Western blotting (FIG. 1B). Importantly, DMOG did not induced change in the RNA binding of TDP43, a well known aggregation-prone RBP (not shown). Next, cells were 254 nm UV-crosslinked (UV-CL) to covalently retain the RNA-protein interactions, then endogenous p62 was immunoprecipitated (IP) and 5' ends of RNAs were phosphor-labeled with T4 polynucleotide kinase (PNK) (FIG. 1C). Importantly, p62-RNA complexes shifted upwards in the SDS-PAGE gel depending on the RNAse concentration pretreatment, confirming that RNA is being phosphorylated. The inventors repeated PNK labeling assay with exogenously expressed FLAG-p62 as well (not shown).

In order to identify the RNA targets of p62, iCLIP (Konig et al., 2010) was employed, which allows for nucleotide-resolution identification of RNA-protein contacts (crosslink sites, CS). Two p62 antibodies (mouse monoclonal and rabbit polyclonal), empty beads and respective isotype controls were used and it was confirmed by proteomics that p62 is indeed the major protein purified giving rise to RNA-dependent phosphor signal. Next, the inventors proceeded with p62 IPs from cells treated with DMOG, or DMSO only, PNK-labeled RNA-protein complexes and confirmed the identity of p62 in purified complexes in high RNAse treated IPs with subsequent Western blotting. After cDNA production, sequencing, uniquely mapping to human genome, filtering and statistical testing 1998 CS (out of ~106 total CS) were found enriched in p62 samples over the controls (FIG. 1D). These sites mostly mapped into tRNAs and tRNA pseudogenes. CS from significant p62 multiple mapped reads (n=5221) fell into 5S rRNA, Y-RNAs, U1 and U6 RNAs. Interestingly, CS were identified also in the primary RNA transcripts of several un-spliced tRNAs indicating that p62 binding to RNA occurs in the nucleus, likely in the vicinity of PolIII transcription. In order to rank p62 interacting RNAs based on enrichment score, the inventors calculated qualitative CS density over the length of bound RNA species. This indicated that 3 out of 4 vault RNAs (vtRNA2-1, vtRNA1-1, vtRNA1-2), are among top enriched p62 interacting RNAs (FIG. 1E). Lastly, comparison of CS quantitative read counts in p62 IPs pointed to few CSs with decreased read values upon DMOG treatment located also in above mentioned vtRNAs (FIG. 1E).

5' and 3' sequences of vault RNAs are highly conserved and form terminal stem loop region, while central domain is dissimilar between all four vtRNA paralogs (Stadler et al., 2009). p62 binding sites on vtRNAs were inspected and it was noted that p62 preferentially bound single stranded loop regions in central domain of vtRNAs species with no apparent sequence specificity (FIG. 1E). Importantly, vtRNAs co-purified in oligo-dT fraction was observed, which potentially explains why p62 appeared in oligo-dT mediated interactome capture despite binding predominantly PolIII targets.

These results show establish p62 as an RNA binding protein that increases its RNA binding upon DMOG treatment and binds restricted set of PolIII transcribed RNAs including vtRNAs.

Example 2: vtRNA1-1 Affects p62 Oligomerization

Since their discovery and realization that all vault RNAs can be found associated to the vault particle (Nandy et al., 2009), the most studied vault RNA is the vtRNA1-1, especially in connections to γ-Herpesvirus infection (Amort et al., 2015). Electro mobility shift assays (EMSA) were used to recapitulate RNA-protein interaction using radioactively labeled vtRNA1-1 and MBP-tagged p62 in vitro. It was observed that vtRNA1-1 interacts with MBP tagged p62, but not with the MBP tag only (FIG. 2A) and that this interaction is susceptible to specific competition of cold labeled vtRNA1-1 (not shown). Apparent Kd of the MBP_p62-vtRNA1-1 complex was in 60 nM range. The RNA-protein complex signal was observed to be immediately below the wells in the EMSA gel, despite the fact that the predicted pI of p62 is 5.1 and that TBE buffer for EMSA (pH8.3) was used.

p62 protein contains domains and motifs with diverse functions (Stolz et al., 2014). PB1 domain is responsible for oligomerization of p62, LIR-motif for the binding to GABARAB/LC-3, MR motif for the interaction with KEAP1 (Komatsu et al., 2010), UBA domain for the binding to poly-ubiquitin, while the ZZ-domain, a degenerate zinc finger, was yet least characterized domain shown to interact with RIP-1 (Sanz et al., 1999). Furthermore, p62 has two nuclear localization signals and nuclear export sequence (Pankiv et al., 2010) (FIG. 2C).

The inventors hypothesized that vtRNA1-1 induced formation of higher order complexes with p62, possibly by inducing oligomerization via PB1 domain, and thus precluding the complex to resolve into gel. Yet, the p62 variant with mutations in critical residues in the PB1 domain (R21A, D69A, D73A) that abolish its polymerization properties, formed complex with vtRNA1-1 in similar nM range and stacked below the gel wells, too (FIG. 2A). This suggested that the vtRNA1-1 may affect the higher order structure of p62 by other means than interaction with PB1 domain. Previously, a linker region between PB1 and ZZ-domain was shown to play an important role in stabilizing p62 polymer-filaments in vitro (Ciuffa et al., 2015). Interestingly, double arginine mutation in that region (R106E, R107E) that prevented filament formation (Ciuffa et al., 2015), also prominently decreased the binding of vtRNA1-1 to p62 (FIG. 2B), suggesting that the linker region could contribute to the RNA binding in vitro.

In order to map the RNA binding residue(s) on p62 (FIG. 2C), the inventors employed RBDmap protocol (Castello et al.). In short, interactome capture proteins crosslinked to polyA+ RNAs were subjected to low frequency protease (LysC) cleavage and enriched second time by oligo-dT beads. RNA cross-linked peptides were further digested with trypsin and analyzed on MS. As the peptide cross-linked to RNA cannot be identified due to the unpredictable mass shift, neighboring peptide (N-link) indicates the vicinity of RNA bound residues (Castello et al.). N-link peptide of p62 fell into the ZZ-domain (FIG. 2D), which is predicted to accommodate zinc atoms via CCCC and CCHH residues. The inventors therefore tested an array of alanine mutations of potential RNA binding amino acid residues proximal and distal of N-link peptide by expressing FLAG-HA tagged variants of p62, followed by UV-crosslinking, IP and PNK labeling. Plasmid transfections-based assay indicated that residues R139 and K141 from the RYK-motif may be involved in RNA binding. This motif is conserved from bullfrog to human and homology modelling projects the residues R139 and K141 outside of ZZ-domain in "aligned" order, which could form a platform for contacts to bound RNA. As endogenous p62 hetero-polymerizes with exogenously expressed mutant p62, it may interfere with the signal evaluation after IP-PNK labeling. The inventors prepared inducible stable cell lines and repeated IP-PNK labeling (FIG. 2E). This indicated the mutation K141A as the one decreasing the binding of p62 to the RNA at most. Next, the relationship of p62 filament formation and RNA binding was investigated in vivo by IP-PNK assay using stable inducible cell lines. PB1 domain mutations did not abrogate RNA binding of p62, while 2RE mutations had no effect on RNA binding of p62, either combined with wt, or with PB1 domain mutations, in contrast to the in vitro data (FIG. 2E). This may reflect differential modes of RNA binding by p62 in vivo, subjected to PTMs or RNP complex properties which cannot be recapitulated in vitro.

Multimerization of p62 can be observed as formation of p62 larger MW bands (doublet, triplet etc.) on PAGE as well as aggregation in stacking gel (Cha-Molstad et al., 2015). These multimers become prominent when UV-CL was applied (not shown). As expected, multimers were not formed when p62 PB1 mutant was used, but were pronounced when p62 K141A mutant was used as compared to wt (FIG. 2F). This inversely correlated with the RNA binding of the monomeric unit (FIG. 2F), suggesting that the RNA binding deficient p62 is more prone for multimerization via PB1 domain.

To further show that residues K141 and R139 of p62 protein are involved in interaction with RNA, the inventors performed experiment depicted in the FIG. 5. First, control or p62 knockdown was performed using siRNAs. Then, the cells were transfected either with empty vector plasmid or plasmids encoding wild-type, or variant p62 proteins, respectively. Afterwards, immunoprecipitation and T4 PNK labeling was performed to assess RNA binding of p62. As observed in the upper right panel of FIG. 5, mutation of residue K141 to alanine decreased the RNA binding of p62, which was further pronounced by the double mutation of K141A/R139A.

Hence, vtRNA1-1 affects higher order formation of p62 by regulating its polymerization properties and induction of "smaller order complexes" with the contribution of the linker region located between PB1 and ZZ-domain.

Example 3: vtRNA1-1 Levels Regulate p62-Dependent Autophagic Flux

As p62 functions in targeted autophagy processes, we initially postulated that its RNA binding activity may reflect involvement in "RNA-phagy" pathway, similar to the ribophagy pathway described in yeast (Kraft et al., 2008). To test this we evaluated vtRNAs levels using Northern blot after protein siRNA knockdown (KD). Next to p62, we knocked down TEP1, which is required for the stability of vtRNAs (Kickhoefer et al., 2001), as well as MVP, a structural component of the vaults, which does not directly interact with vtRNA. KD of p62 (FIG. 3A) led to decrease of the steady state levels of vtRNA1-1 and to lesser extent also of vtRNA1-2, while the vtRNA1-3 and vtRNA2-1, or control tRNALys and 5S rRNA seemed unaffected (FIG. 4B). As expected, TEP1 KD affected stability of all vtRNA species except vtRNA1-3, while Scr or MVP KD did not affect vtRNAs levels (FIG. 3B). Thus, p62 is not required for the degradation of vtRNAs.

The inventors then focused on vtRNA1-1 and observed that its KD using LNAs led to decrease in TEP1 and MVP protein levels, possibly due to the interaction of these components in vault complex (FIG. 3C, D). Interestingly, depletion of vtRNA1-1 also resulted in decrease in p62 levels and pronounced LC3B conjugation (FIG. 3C, D), and increased formation of p62 punctae (FIG. 3E), suggesting increased autophagic flux. Conversely, the inventors inspected autophagy flux in cells with overexpression of vtRNA1-1 by inducible H1 promoter containing plasmid, which led to increase in p62 levels and markedly decreased LC3B conjugation (FIG. 3F). vtRNA1-1 overexpression could also reverse the LNA KD phenotype as measured by LC3B conjugation, albeit to a lower extent. These experiments suggested that the level of vtRNA1-1 affects basal autophagy flux.

Next the inventors investigated whether the impact of vtRNA1-1 on autophagy is dependent on p62. Concurrent KD of p62 and vtRNA1-1 diminished the conjugation effects on LC3B as compared to the Scr siRNA treated samples (FIG. 3G). Bafilomycine A1 treatment showed no difference in conjugated LC3B levels between negA and vtRNA1-1 LNAs treated cells, indicating that the vtRNA1-1 does not affect autophagy at the autophagosomal turnover stage (FIG. 3G). Thus, vtRNA1-1 mediates its effects on autophagy flux via p62.

vtRNA1-1 is an integral component of vault particles and its KD affected the levels of MVP as well (see FIG. 3D, G). Yet, it was reported that only about 20% of vtRNA1-1 is associated with the vaults, while the rest is in free cytoplasm (Nandy et al., 2009). Therefore the inventors isolated vaults using 100,000 g centrifugation from cells treated with p62, TEP1 or MVP siRNA and observed that vaults are formed also in TEP1 and p62 deficient cells (FIG. 3H). Also, majority of TEP1 is not associated with the vaults (FIG. 3H), implying for function of vtRNA1-1-TEP1 complex outside of vault particle.

Example 4: vtRNA1-1 Specifically Modulates Autophagy

To assess, whether the regulatory potential of vault RNA1-1 on p62-mediated autophagy is also observed by other vault RNAs or is specific to the vtRNA1-1, the authors transfected the cells with control plasmid or plasmids encoding different vault RNAs, respectively, and assayed the autophagy by inspection of the LC3B conjugation. FIG. 6A shows quantification of several independent experiments where LC3B conjugation is affected significantly by the overexpression of the vault RNA1-1, but not by the other vault RNAs. Importantly, upon treatment with bafilomycine A1, the LC3B conjugation ratio was restored, which showed a restriction in the autophagy flux, rather than a defect in the conjugation process. To control the levels of the overexpressed vault RNAs, the authors isolated the total RNA from transfected cells and inspected their levels by Northern blotting, as shown in the FIG. 6B.

Example 5: p62 is Required for the Vault RNA1-1-Mediated Effects on Autophagy

To show, that the vault RNA1-1 effects on the autophagy are mediated via p62, the authors used control or p62 siRNA transfections combined with the LNA mediated knockdown of control or vault RNA1-1. Alternatively, LNA knockdown cells were treated with bafilomycine A1. FIG. 6C shows, that LNA mediated knockdown impacts on autophagy as observed by the decrease in p62 levels and increased conjugation of LC3B (compare lanes 1 and 2). Next, removal of p62 diminished the effect of the vault RNA knockdown on LC3B conjugation (compare lanes 2 and 4), confirming that p62 is required for the vault RNA1-1-mediated effects on autophagy. Lastly, treatment with bafilomycine A1 restored the relative levels between the LC3B-I and LC3B-II species (compare lanes 5 and 6), confirming that vault RNA1-1 does not inhibit autophagosome-lysosome phusion, but rather increase the autophagy flux.

Example 6: RNA Binding is Responsible for p62's Role in Autophagy

In order to establish a relationship between the RNA binding of p62 and its role in autophagy, the authors starved the cells and assayed the RNA binding of p62 by T4 PNK labeling of p62 immuno-precipitates. This experiment, depicted in FIG. 6D, showed that during the course of autophagy, when p62 is actively contributing in clearing cytosolic cargos, its RNA binding gradually decreases. This established an inverse relationship between p62 RNA binding activity and its autophagy potential. Next, authors inspected the levels of vault RNA1-1 in the course of starvation and observed, that the levels of vault RNA1-1 were gradually decreasing (FIG. 6D). This experiment showed that starvation causes a removal of p62 inhibitor (vault RNA1-1) and establishes a causal link between the levels of vault RNA1-1 and p62 RNA binding.

Collectively, p62 RNA binding is not required for autophagic clearance of vault RNA or vaults, but rather vtRNA1-1 serves as a negative regulator of autophagy flux via p62 prior to the autophagosomes-lysosomes fusion. Further, removal of vaults also affects autophagy.

REFERENCES

Amort, M., Nachbauer, B., Tuzlak, S., Kieser, A., Schepers, A., Villunger, A., and Polacek, N. (2015). Expression of the vault RNA protects cells from undergoing apoptosis. Nature communications 6, 7030.

Baltz, A. G., Munschauer, M., Schwanhausser, B., Vasile, A., Murakawa, Y., Schueler, M., Youngs, N., Penfold-Brown, D., Drew, K., Milek, M., et al. (2012). The mRNA-bound proteome and its global occupancy profile on protein-coding transcripts. Molecular cell 46, 674-690.

Beckmann, B. M., Horos, R., Fischer, B., Castello, A., Eichelbaum, K., Alleaume, A. M., Schwarzl, T., Curk, T., Foehr, S., Huber, W., et al. (2015). The RNA-binding proteomes from yeast to man harbour conserved enigmRBPs. Nature communications 6, 10127.

Berger, W., Steiner, E., Grusch, M., Elbling, L., and Micksche, M. (2009). Vaults and the major vault protein: novel roles in signal pathway regulation and immunity. Cellular and molecular life sciences: CMLS 66, 43-61.

Castello, A., Fischer, B., Eichelbaum, K., Horos, R., Beckmann, B. M., Strein, C., Davey, N. E., Humphreys, D. T., Preiss, T., Steinmetz, L. M., et al. (2012). Insights into RNA biology from an atlas of mammalian mRNA-binding proteins. Cell 149, 1393-1406.

Cavignac, Y., and Esclatine, A. (2010). Herpesviruses and autophagy: catch me if you can! Viruses 2, 314-333.

Cech, T. R., and Steitz, J. A. (2014). The noncoding RNA revolution-trashing old rules to forge new ones. Cell 157, 77-94.

Cha-Molstad, H., Sung, K. S., Hwang, J., Kim, K. A., Yu, J. E., Yoo, Y. D., Jang, J. M., Han, D. H., Molstad, M., Kim, J. G., et al. (2015). Amino-terminal arginylation targets endoplasmic reticulum chaperone BiP for autophagy through p62 binding. Nature cell biology 17, 917-929.

Ciuffa, R., Lamark, T., Tarafder, A. K., Guesdon, A., Rybina, S., Hagen, W. J., Johansen, T., and Sachse, C. (2015). The selective autophagy receptor p62 forms a flexible filamentous helical scaffold. Cell reports 11, 748-758.

Duran, A., Amanchy, R., Linares, J. F., Joshi, J., Abu-Baker, S., Porollo, A., Hansen, M., Moscat, J., and Diaz-Meco, M. T. (2011). p62 is a key regulator of nutrient sensing in the mTORC1 pathway. Molecular cell 44, 134-146.

Duran, R. V., MacKenzie, E. D., Boulahbel, H., Frezza, C., Heiserich, L., Tardito, S., Bussolati, O., Rocha, S., Hall, M. N., and Gottlieb, E. (2013). HIF-independent role of prolyl hydroxylases in the cellular response to amino acids. Oncogene 32, 4549-4556.

Duran, R. V., Oppliger, W., Robitaille, A. M., Heiserich, L., Skendaj, R., Gottlieb, E., and Hall, M. N. (2012). Glutaminolysis activates Rag-mTORC1 signaling. Molecular cell 47, 349-358.

Itakura, E., and Mizushima, N. (2011). p62 Targeting to the autophagosome formation site requires self-oligomerization but not LC3 binding. The Journal of cell biology 192, 17-27.

Karve, T. M., and Cheema, A. K. (2011). Small changes huge impact: the role of protein posttranslational modifications in cellular homeostasis and disease. J Amino Acids 2011, 207691.

Kedersha, N. L., and Rome, L. H. (1986). Isolation and characterization of a novel ribonucleoprotein particle: large structures contain a single species of small RNA. The Journal of cell biology 103, 699-709.

Kickhoefer, V. A., Liu, Y., Kong, L. B., Snow, B. E., Stewart, P. L., Harrington, L., and Rome, L. H. (2001). The Telomerase/vault-associated protein TEP1 is required for vault RNA stability and its association with the vault particle. The Journal of cell biology 152, 157-164.

Kim, J., Kundu, M., Viollet, B., and Guan, K. L. (2011). AMPK and mTOR regulate autophagy through direct phosphorylation of Ulk1. Nature cell biology 13, 132-141.

Klionsky, D. J., Abdalla, F. C., Abeliovich, H., Abraham, R. T., Acevedo-Arozena, A., Adeli, K., Agholme, L., Agnello, M., Agostinis, P., Aguirre-Ghiso, J. A., et al. (2012). Guidelines for the use and interpretation of assays for monitoring autophagy. Autophagy 8, 445-544.

Komatsu, M., Kurokawa, H., Waguri, S., Taguchi, K., Kobayashi, A., Ichimura, Y., Sou, Y. S., Ueno, I., Sakamoto, A., Tong, K. I., et al. (2010). The selective autophagy substrate p62 activates the stress responsive transcription factor Nrf2 through inactivation of Keap1. Nature cell biology 12, 213-223.

Kong, L. B., Siva, A. C., Kickhoefer, V. A., Rome, L. H., and Stewart, P. L. (2000). RNA location and modeling of a WD40 repeat domain within the vault. RNA 6, 890-900.

Konig, J., Zarnack, K., Rot, G., Curk, T., Kayikci, M., Zupan, B., Turner, D. J., Luscombe, N. M., and Ule, J. (2010). iCLIP reveals the function of hnRNP particles in splicing at individual nucleotide resolution. Nature structural & molecular biology 17, 909-915.

Kraft, C., Deplazes, A., Sohrmann, M., and Peter, M. (2008). Mature ribosomes are selectively degraded upon starvation by an autophagy pathway requiring the Ubp3p/Bre5p ubiquitin protease. Nature cell biology 10, 602-610.

Li, F., Chen, Y., Zhang, Z., Ouyang, J., Wang, Y., Yan, R., Huang, S., Gao, G. F., Guo, G., and Chen, J. L. (2015). Robust expression of vault RNAs induced by influenza A virus plays a critical role in suppression of PKR-mediated innate immunity. Nucleic Acids Res 43, 10321-10337.

Mancias, J. D., Wang, X., Gygi, S. P., Harper, J. W., and Kimmelman, A. C. (2014). Quantitative proteomics identifies NCOA4 as the cargo receptor mediating ferritinophagy. Nature 509, 105-109.

Nandy, C., Mrazek, J., Stoiber, H., Grasser, F. A., Huttenhofer, A., and Polacek, N. (2009). Epstein-barr virus-induced expression of a novel human vault RNA. J Mol Biol 388, 776-784.

Pankiv, S., Lamark, T., Bruun, J. A., Overvatn, A., Bjorkoy, G., and Johansen, T. (2010). Nucleocytoplasmic shuttling of p62/SQSTM1 and its role in recruitment of nuclear polyubiquitinated proteins to promyelocytic leukemia bodies. The Journal of biological chemistry 285, 5941-5953.

Rogov, V., Dotsch, V., Johansen, T., and Kirkin, V. (2014). Interactions between autophagy receptors and ubiquitin-like proteins form the molecular basis for selective autophagy. Molecular cell 53, 167-178.

Sanz, L., Sanchez, P., Lallena, M. J., Diaz-Meco, M. T., and Moscat, J. (1999). The interaction of p62 with RIP links the atypical PKCs to NF-kappaB activation. The EMBO journal 18, 3044-3053.

Shimobayashi, M., and Hall, M. N. (2016). Multiple amino acid sensing inputs to mTORC1. Cell Res 26, 7-20.

Sica, V., Galluzzi, L., Bravo-San Pedro, J. M., Izzo, V., Maiuri, M. C., and Kroemer, G. (2015). Organelle-Specific Initiation of Autophagy. Molecular cell 59, 522-539.

Stadler, P. F., Chen, J. J., Hackermuller, J., Hoffmann, S., Horn, F., Khaitovich, P., Kretzschmar, A. K., Mosig, A., Prohaska, S. J., Qi, X., et al. (2009). Evolution of vault RNAs. Mol Biol Evol 26, 1975-1991.

Stolz, A., Ernst, A., and Dikic, I. (2014). Cargo recognition and trafficking in selective autophagy. Nature cell biology 16, 495-501.

Tan, C. Y., and Hagen, T. (2013). Post-translational regulation of mTOR complex 1 in hypoxia and reoxygenation. Cellular signalling 25, 1235-1244.

Webb, J. D., Coleman, M. L., and Pugh, C. W. (2009). Hypoxia, hypoxia-inducible factors (HIF), HIF hydroxylases and oxygen sensing. Cellular and molecular life sciences: CMLS 66, 3539-3554.

Zhang, J., Gao, Z., Yin, J., Quon, M. J., and Ye, J. (2008). S6K directly phosphorylates IRS-1 on Ser-270 to promote insulin resistance in response to TNF-(alpha) signaling through IKK2. The Journal of biological chemistry 283, 35375-35382.

The invention claimed is:

1. A method for modulating autophagy flux in a cell, comprising a step of inhibiting or increasing interaction of a vault RNA (vtRNA) and p62 in the cell,
   a step of monitoring the interaction of the vtRNA and p62 in the cell, and/or
   a step of determining the autophagic flux in the cell by monitoring modulation of conjugation of microtubule-associated protein 1A/1B-light chain 3 (LC3) and/or formation of p62 punctae in the cell,
wherein inhibiting the interaction of a vault RNA (vtRNA) and p62 in the cell increases the autophagic flux in the cell, whereas increasing the interaction of a vault RNA (vtRNA) and p62 in the cell decreases the autophagy flux in the cell.

2. The method according to claim 1, wherein the modulation of autophagy is a modulation of the autophagy flux in the cell.

3. The method according to claim 1, wherein inhibiting or enhancing the interaction of a vtRNA and p62 in the cell is accomplished by contacting said cell with an antagonist or agonist of the expression, function or stability of a vtRNA.

4. The method according to claim 1, wherein inhibiting or increasing the interaction of a vtRNA and p62 in the cell is accomplished by contacting said cell with an substance capable of competitively disturbing, or enhancing, the binding between the vtRNA and p62, preferably wherein said substance binds to a region of p62 comprising R139 and/or K141.

5. The method according to claim 1, wherein the vtRNA is selected from, vtRNA1-1 (SEQ ID NO: 3), vtRNA1-2 (SEQ ID NO: 4), vtRNA1-3 (SEQ ID NO: 5) and vtRNA2-1 (SEQ ID NO: 6), and preferably is vtRNA1-1 (SEQ ID NO: 3).

6. The method according to claim 3, wherein an antagonist of a vtRNA is an antisense nucleic acid targeting the sequence of the vtRNA, such as an siRNA, LNA, shRNA, or other antisense RNA interfering oligonucleotide, and wherein an agonist of a vtRNA is an expression construct of the vtRNA, preferably wherein the expression construct comprises a vtRNA sequence operably linked to an expression promoter.

* * * * *

```
                       SEQUENCE LISTING

<160> NUMBER OF SEQ ID NOS: 14

<210> SEQ ID NO 1
<211> LENGTH: 16
<212> TYPE: DNA
<213> ORGANISM: artificial
<220> FEATURE:
<223> OTHER INFORMATION: LNA

<400> SEQUENCE: 1
ttaaagaact gtcgaa                                                    16

<210> SEQ ID NO 2
<211> LENGTH: 15
<212> TYPE: DNA
<213> ORGANISM: artificial
<220> FEATURE:
<223> OTHER INFORMATION: LNA

<400> SEQUENCE: 2
ttaaagaact gtcga                                                     15

<210> SEQ ID NO 3
<211> LENGTH: 98
<212> TYPE: RNA
<213> ORGANISM: Homo sapiens

<400> SEQUENCE: 3
ggcuggcuuu agcucagcgg uuacuucgac aguucuuuaa uugaaacaag caaccugucu    60
ggguuguucg agacccgcgg gcgcucucca guccuuuu                            98

<210> SEQ ID NO 4
<211> LENGTH: 88
<212> TYPE: RNA
<213> ORGANISM: Homo sapiens

<400> SEQUENCE: 4
ggcuggcuuu agcucagcgg uuacuucgag uacauuguaa ccaccucucu gggugguucg    60
agacccgcgg gugcuuucca gcucuuuu                                       88

<210> SEQ ID NO 5
```

<210> SEQ ID NO 5
<211> LENGTH: 88
<212> TYPE: RNA
<213> ORGANISM: Homo sapiens

<400> SEQUENCE: 5
ggcuggcuuu agcucagcgg uuacuucgcg ugucaucaaa ccaccucucu ggguuguucg    60
agacccgcgg gcgcucucca gcccucuu                                      88

<210> SEQ ID NO 6
<211> LENGTH: 100
<212> TYPE: RNA
<213> ORGANISM: Homo sapiens

<400> SEQUENCE: 6
gggucggagu uagcucaagc gguuaccucc ucaugccgga cuuucuaucu guccaucucu    60
gugcuggggu ucgagacccg cgggugcuua cugacccuuu                         100

<210> SEQ ID NO 7
<211> LENGTH: 98
<212> TYPE: DNA
<213> ORGANISM: Homo sapiens

<400> SEQUENCE: 7
ggctggcttt agctcagcgg ttacttcgac agttctttaa ttgaaacaag caacctgtct    60
gggttgttcg agacccgcgg gcgctctcca gtccttt                             98

<210> SEQ ID NO 8
<211> LENGTH: 88
<212> TYPE: DNA
<213> ORGANISM: Homo sapiens

<400> SEQUENCE: 8
ggctggcttt agctcagcgg ttacttcgag tacattgtaa ccacctctct gggtggttcg    60
agacccgcgg gtgctttcca gctcttt                                        88

<210> SEQ ID NO 9
<211> LENGTH: 88
<212> TYPE: DNA
<213> ORGANISM: Homo sapiens

<400> SEQUENCE: 9
ggctggcttt agctcagcgg ttacttcgcg tgtcatcaaa ccacctctct gggttgttcg    60
agacccgcgg gcgctctcca gccctctt                                       88

<210> SEQ ID NO 10
<211> LENGTH: 100
<212> TYPE: DNA
<213> ORGANISM: Homo sapiens

<400> SEQUENCE: 10
gggtcggagt tagctcaagc ggttacctcc tcatgccgga ctttctatct gtccatctct    60
gtgctggggt tcgagacccg cgggtgctta ctgacccttt                         100

<210> SEQ ID NO 11
<211> LENGTH: 66
<212> TYPE: PRT
<213> ORGANISM: Homo spaiens

<400> SEQUENCE: 11

Tyr Ile Lys Glu Lys Lys Glu Cys Arg Arg Asp His Arg Pro Pro Cys

```
                1               5                   10                  15
Ala Gln Glu Ala Pro Arg Asn Met Val His Pro Asn Val Ile Cys Asp
            20                  25                  30

Gly Cys Asn Gly Pro Val Val Gly Thr Arg Tyr Lys Cys Ser Val Cys
        35                  40                  45

Pro Asp Tyr Asp Leu Cys Ser Val Cys Glu Gly Lys Gly Leu His Arg
    50                  55                  60

Gly His
65

<210> SEQ ID NO 12
<211> LENGTH: 66
<212> TYPE: PRT
<213> ORGANISM: Mus musculus

<400> SEQUENCE: 12

Tyr Ile Lys Glu Lys Lys Glu Cys Arg Arg Glu His Arg Pro Pro Cys
1               5                   10                  15

Ala Gln Glu Ala Pro Arg Asn Met Val His Pro Asn Val Ile Cys Asp
            20                  25                  30

Gly Cys Asn Gly Pro Val Val Gly Thr Arg Tyr Lys Cys Ser Val Cys
        35                  40                  45

Pro Asp Tyr Asp Leu Cys Ser Val Cys Glu Gly Lys Gly Leu His Arg
    50                  55                  60

Glu His
65

<210> SEQ ID NO 13
<211> LENGTH: 66
<212> TYPE: PRT
<213> ORGANISM: Lithobates catesbeiana

<400> SEQUENCE: 13

Tyr Ile Lys Glu Arg Lys Glu Cys Lys Arg Asp His Arg Gly His Cys
1               5                   10                  15

Gly Gln Glu Thr Pro Gln Asn Val Val His Pro Asn Val Thr Cys Asp
            20                  25                  30

Gly Cys Asp Gly Pro Val Val Gly Asn Arg Phe Lys Cys Leu Ile Cys
        35                  40                  45

Pro Asp Tyr Asp Leu Cys Ser Thr Cys Glu Lys Lys Gly Ile His Lys
    50                  55                  60

Glu His
65

<210> SEQ ID NO 14
<211> LENGTH: 53
<212> TYPE: PRT
<213> ORGANISM: Danio rerio

<400> SEQUENCE: 14

Phe Ile Lys Gln Arg Lys Glu His Lys Arg Asp Val His Pro Gly Val
1               5                   10                  15

Thr Cys Asp Gly Cys Asp Gly Pro Val Ala Gly Thr Arg Tyr Lys Cys
            20                  25                  30
```

Thr Val Cys Pro Asp Tyr Asp Leu Cys Pro Thr Cys Gln Ser Lys Gly
        35                  40                  45

Leu His Lys Glu His
    50